(12) United States Patent
Selch

(10) Patent No.: US 7,632,255 B2
(45) Date of Patent: Dec. 15, 2009

(54) SUBPALPEBRAL LAVAGE CATHETER DEVICE

(76) Inventor: Andrea H. Selch, 2916 Ericka Dr., Hillsborough, NC (US) 27278

( * ) Notice: Subject to any disclaimer, the term of this patent is extended or adjusted under 35 U.S.C. 154(b) by 238 days.

(21) Appl. No.: 11/208,118

(22) Filed: Aug. 19, 2005

(65) Prior Publication Data

US 2007/0078384 A1  Apr. 5, 2007

(51) Int. Cl.
- *A61M 1/00* (2006.01)
- *A61M 31/00* (2006.01)
- *A61M 37/00* (2006.01)
- *A61M 35/00* (2006.01)
- *A61K 9/02* (2006.01)
- *A61F 13/12* (2006.01)

(52) U.S. Cl. ............ 604/317; 604/48; 604/500; 604/93.01; 604/289; 604/294; 604/298; 604/300; 602/74

(58) Field of Classification Search ......... 604/174, 604/179, 180, 177, 178, 29, 283, 83–86, 604/284, 905, 94, 48, 500, 93.01, 289, 294, 604/298, 300, 317; 2/96, 256, 260, 410, 2/4, 423; 602/74
See application file for complete search history.

(56) References Cited

U.S. PATENT DOCUMENTS

| | | | |
|---|---|---|---|
| RE28,873 E |  | 6/1976 | Morgan |
| 4,562,794 A | * | 1/1986 | Speckman ............ 119/651 |
| 4,570,688 A | * | 2/1986 | Williams ............ 150/134 |
| 4,582,508 A |  | 4/1986 | Pavelka |
| 4,699,613 A | * | 10/1987 | Donawick et al. ......... 604/80 |
| 5,271,745 A |  | 12/1993 | Fentress et al. |
| 5,664,581 A |  | 9/1997 | Ashley |
| 5,755,698 A |  | 5/1998 | Kagan et al. |
| 5,765,548 A | * | 6/1998 | Perry ............ 128/200.24 |
| 5,839,393 A |  | 11/1998 | Rupp et al. |
| 6,224,571 B1 |  | 5/2001 | Bierman |
| 6,497,683 B1 |  | 12/2002 | Pagni |
| 6,669,682 B1 | * | 12/2003 | Gibson et al. ........... 604/890.1 |
| 7,201,739 B2 |  | 4/2007 | Walborn |

(Continued)

FOREIGN PATENT DOCUMENTS

GB  185616 A  9/1922

OTHER PUBLICATIONS

Horse grooming online forum, accessed Dec. 31, 2008. http://www.horsegroomingsupplies.com/horse-chat-forum/get_topic/1/000485.html.*

(Continued)

*Primary Examiner*—Leslie R Deak
*Assistant Examiner*—Adam Marcetich
(74) *Attorney, Agent, or Firm*—Michael G. Johnston; Deborah H. Spencer; Moore & Van Allen PLLC

(57) ABSTRACT

A subpalpebral lavage catheter device for a mammal comprising a subpalpebral catheter having a first and a second end wherein the first end is located under the skin of the mammal and the second end further comprises an injection port, a hollow pouch, wherein the pouch has an opening adapted to receive the injection port of the catheter, a means for closing the opening of said pouch, and a plurality of loops attached to a side of the pouch, spaced apart and of a length wherein the loops are adapted to be braided into hair of the mammal.

29 Claims, 3 Drawing Sheets

U.S. PATENT DOCUMENTS

| | | | |
|---|---|---|---|
| 2002/0128613 A1* | 9/2002 | Nakayama | 604/294 |
| 2002/0177838 A1* | 11/2002 | Germain | 604/500 |
| 2003/0070674 A1* | 4/2003 | Perry et al. | 128/200.14 |
| 2003/0150457 A1* | 8/2003 | Miller et al. | 128/204.18 |
| 2004/0082916 A1 | 4/2004 | Jenkins | |
| 2004/0193210 A1 | 9/2004 | Blach et al. | |

OTHER PUBLICATIONS

Elizabeth A. Giuliano, David J. Maggs, Cecil P. Moore, Lisa A. Boland Erin S. Champagne Laurence E. Galle. "Inferomedial placement of a single-entry subpalpebral lavage tube for treatment of equine eye disease." Veterinary Ophthalmology. vol. 3 Issue 2-3, pp. 153-156.*

Andrea H. Selch, International Patent Application No. PCT/US 06/31696 (filing date Aug. 14, 2006), International Search Report and Written Opinion, dated Apr. 24, 2007.

Andrea H. Selch, International Patent Application No. PCT/US 06/31696 (filing date Aug. 14, 2006), International Preliminary Report on Patentability (with Written Opinion), dated Feb. 28, 2008.

Giuliano, E.A. Inferomedial placement of a sing-entry subpalpebral lavage tube for treatment of equine eye disease. Veterinary Ophthalmology. 2000, vol. 3, p. 153-156.

Andrea H. Selch, European Patent Application No. EP 06 81 3433 (filing date Aug. 14, 2006), Supplementary European Search Report, dated Apr. 29, 2009.

* cited by examiner

SUBPALPEBRAL LAVAGE CATHETER DEVICE

FIELD OF THE INVENTION

The invention relates to catheter devices in general. More particularly, the invention pertains to an improved device to protect the injection port of a subpalpebral lavage catheter tube of the type used on a horse.

BACKGROUND OF THE INVENTION

Horses sometimes require medicines to be applied to their eyes to treat any one or more of a number of ailments. The treatment can occur several times a day and extend over a period of several days or weeks. Often, a horse will object to the intrusion of the eye by a veterinarian or owner, and can respond with violent or other erratic behavior. For the safety of the owner and the horse, a subpalpebral lavage system is sometimes employed to provide a way of remotely administering the medication to the horse's eye easily and efficiently. The subpalpebral lavage system is made from a flexible tube having two ends, the first end of which mounts a catheter which is passed through the upper eyelid into the upper conjunctival fornix (the space located between the eyelid and the eye). Medication is introduced to the system through the second end of the tube at a second distant injection port and is delivered to the upper conjunctival fornix of the eye through the tubing with the assistance of air injected into the system to move the medication through the tubing to the eye. Upon reaching the end of the tubing in the upper conjunctival fornix, medication exits the system and runs over the eye.

According to present practice, the injection port at the second end of the tube is allowed to hang freely, or the owner may be instructed to tangle the injection port into the mane of the horse. These practices present a variety of problems, including the opportunity for portions of the tube to become caught by a tree branch or other protrusion such as a board, nail, or bucket, and rip the injection port, the catheter, or portions of the tube out of position, causing pain to the animal and requiring reinsertion of the catheter or rearrangement of the tube. Another common problem is that the injection port becomes dirty or is otherwise contaminated by reason of the animal rolling on the ground, which may require cleaning before its reuse, or worse, the dirt or other contaminate may travel through the tube to the injured eye so as to cause infection or introduce a fungus.

Other attempts have been made to address the problems referred to above with other animals including cats, dogs, and mice. One such method is shown in U.S. patent application Ser. No. 2002/0128613 ("Nakayama"), where a somewhat constricting mesh wrap is used to hold the injection port to the back of a small animal such as a cat, dog or mouse. The mesh wrap of Nakayama is however not suited for use on a large animal, such as a horse, and is deemed to be impractical in general due to the natural objection by animals to wearing such a constricting device. Further, the mesh wrap device of Nakayama permits its injection port to be trapped against the body of the animal which encourages contamination due to dirt and sweat being trapped between the wrap and the injection port, which in turn requires removal of the wrap and cleaning of the injection port. A similar item for a horse is known by the tradename Sleazy Sleepwear, however it presents similar problems as described above, with reference to the Nakayama device.

Another attempt to protect the injection port of a medicating device, while not used with an eye catheter, is described in U.S. Pat. No. 5,839,393 ("Rupp"). In this case, a hard plastic shell is employed to protect the injection port from being pulled loose and moved against the animal's body. However, the Rupp device does not keep the injection port clean. Further, use of a device such as the Rupp device is completely impractical on a large animal, since the animal's legs necessarily have to stick through openings in Rupp's hard plastic shell and risk damage.

SUMMARY OF THE INVENTION

The present invention addresses the foregoing shortcomings and inherent problems of the prior art by providing a device for protecting the injection port of a subpalpebral lavage system. The device comprises a pouch, which is sealed on all sides except one. The open side of the pouch mounts a closeable flap, which allows for insertion and removal of the injection port. The pouch has two or more loops attached to one of its sides and which are removably secured to the horse by braiding two or more of loops through the mane hair of the animal.

The injection port of the catheter tube is normally stored in the pouch when not in use, with the flap in its closed position, but in a manner allowing for a small opening for the tube to pass through. When the medicine or wash is administered to the horse, the flap is unsecured and opened and the injection port is removed from the pouch. After administering the medicine or wash, the process is reversed, keeping the injection port clean and protected between uses.

The foregoing and additional features and advantages will become further apparent from the detailed description that follows.

DETAILED DESCRIPTION

Figure 1:
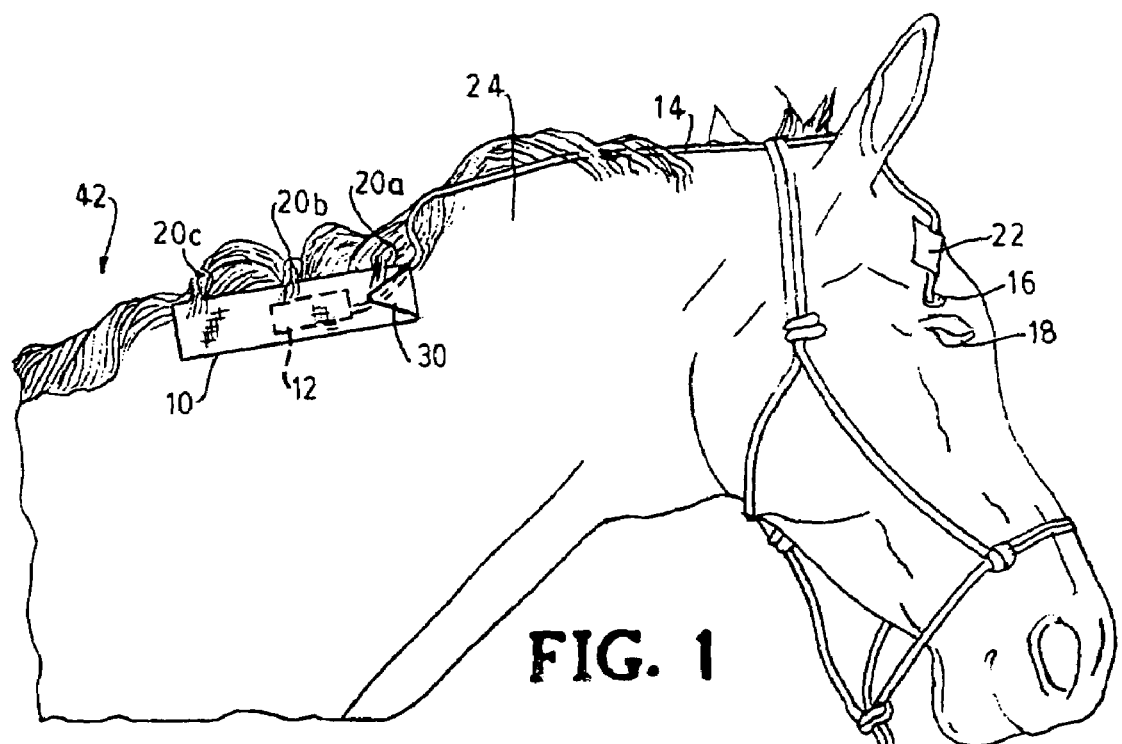
FIG. 1 is a side view of the invention as used on a horse.

FIG. 1 is a side view of the pouch 10 as used on a horse 42 with the loops 20a, 20b, 20c braided into the mane 26 of the horse 42. The subpalpebral lavage catheter tube 14 enters the skin of the horse 16 behind the injured eye 18 and runs down the length of the neck 24 and ends at the injection port 12 contained inside the pouch 10. The catheter tube 14 is attached to the horse's head behind the eyelid by means of a piece of adhesive tape 22.

Figure 2:
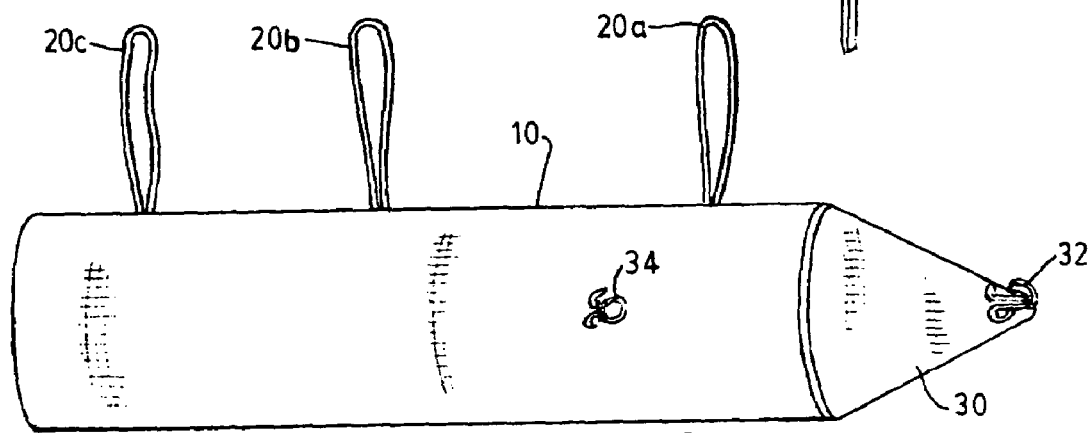
FIG. 2 is a side view of the invention dismounted from the horse with the pouch flap in the open position.

FIG. 2 is a side view of the pouch 10, not attached to a horse, with the flap 30 in the open position, ready to receive the injection port 12 of the catheter tube 14. Longitudinally spaced loops 20a, 20b, 20c are attached to the side 11 of the pouch 10 for braiding into the horse's mane as shown in FIG. 1. The length D of loops 20a, 20b, 20c and the spacings S-1, S-2 are selected and arranged so as to permit such braiding. The hook 32 positioned as in FIG. 2 is not connected to the ring 34 allowing the flap 30 to be open and free to accept the insertion and withdrawal of the injection port (shown in FIG. 3). The length D of loops 20a, 20b, and 20c is approximately two inches in the example being used for reference.

Figure 3:
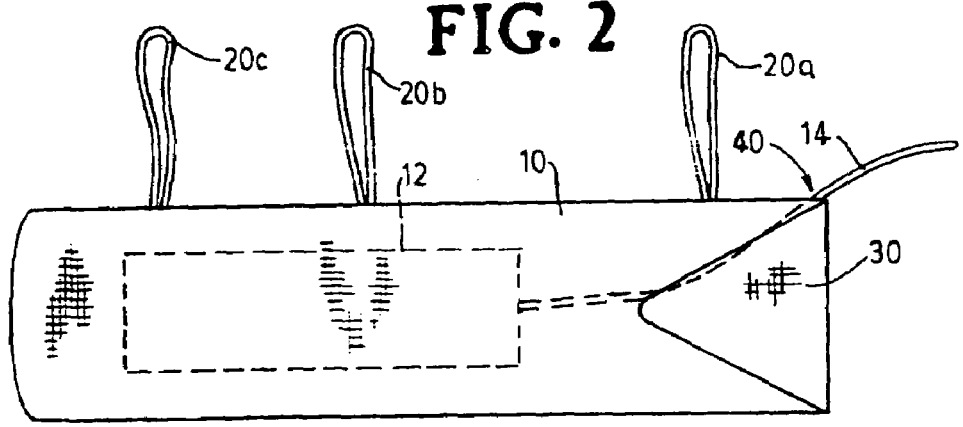
FIG. 3 is a side view of the invention with the pouch flap in the closed position and showing the tube passing through a small opening between the flap and the pouch.

FIG. 3 is a side view of the pouch 10, not attached to a horse, with the flap 30 in the closed position. Loops 20a, 20b, 20c are attached to the side 11 of the pouch 10 for braiding into the horse's mane as shown in FIG. 1. In FIG. 3, The injection port 12 is shown inside the pouch and the catheter tube 14 as shown in FIG. 3, runs to a corner of the pouch 40, where the flap 30 folds, and tube 14 exits the pouch through a small opening 13. The hook is connected to the ring (not shown) that holds the flap securely in the closed position.

The illustrated pouch is formed from a canvas or other suitable resilient material with a length L of approximately eight inches and a width W of approximately one and a half inches. The pouch 10 may be of any other suitable dimension large enough to receive a catheter injection port. Optionally it may be constructed with drainage holes, to eliminate the occasion that water or other liquid should inadvertently enter the pouch. The flap 30 is held in the closed position by the illustrated hook 32 and eye or ring 34 (also known as a "hook and eye"), but many other means may be employed such as Velcro™, a button and hole, toggle, zipper, or drawstring. The only restriction is that there must be at least a small opening at the closed end of the pouch 10 so as to enable the catheter tube to run from the injection port to the horse's neck area.

Figure 4:
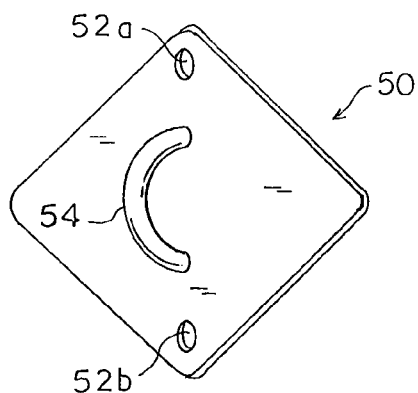
FIG. 4 is a perspective view of a suture wing that may be used according to an embodiment of the invention.

FIG. 4 is a view of a suture wing 50 that may be used in the present invention. The suture wing 50 shown in FIG. 4 has openings 52 through which the suture wing can be removably attached to a mammal and/or a pouch. The suture wing 50 shown in FIG. 4 also has an optional loop structure 54 that may be used to removably attach the suture wing to a desired structure or framework.

Figure 5:
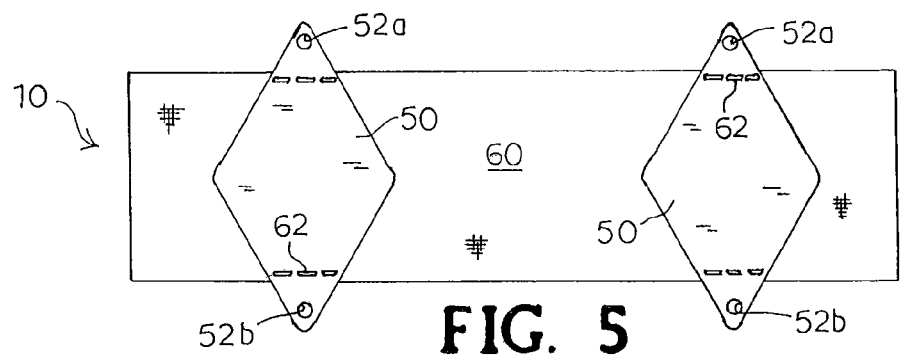
FIG. 5 is a rear plan view of the invention shown with suture wings attached.

FIG. 5 is a view of the pouch 10 of the invention shown with suture wings 50 attached. The pouch 10 is attached to the body of the suture wing 50 by means of stitches 62, thereby leaving the suture wing openings 52 free for use in securing the suture wing and attached pouch to a mammal.

Figure 6:
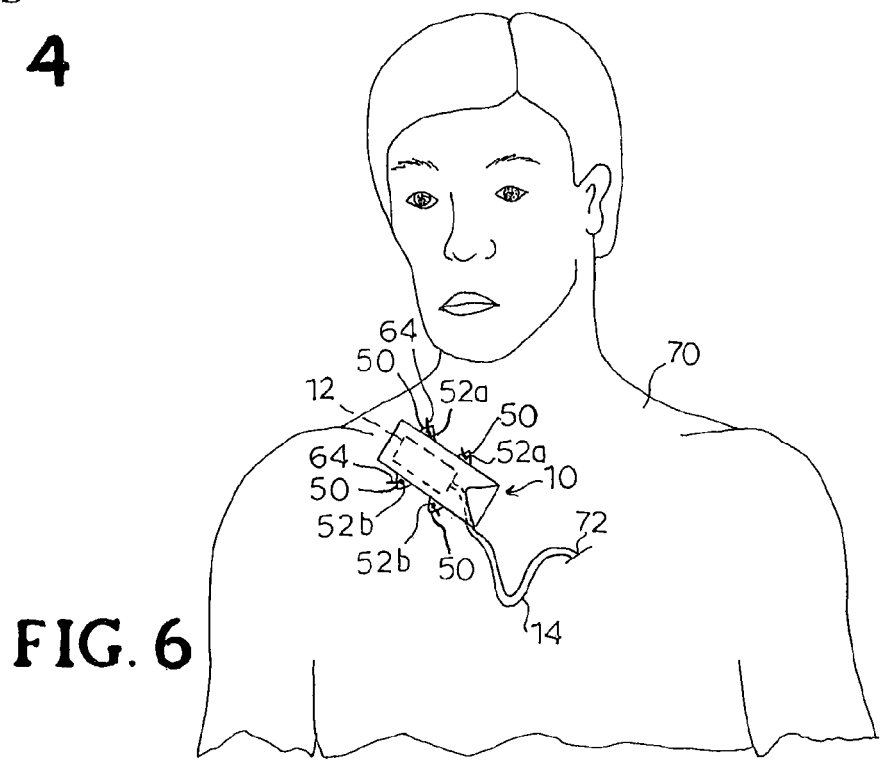
FIG. 6 is a perspective view of the invention as shown in FIG. 5 as may be used on a human.

FIG. 6 is a view of the invention as used on a human 70. The pouch 10 is secured to the torso of a human 70 by means of stitches 64 sewn through the suture wing openings 52 and into the humans skin. The catheter tube 14 runs from the point of insertion into the human torso 72 to the pouch 10 of the invention, wherein the injection port 12 is enclosed within the pouch 10.

Figure 7:
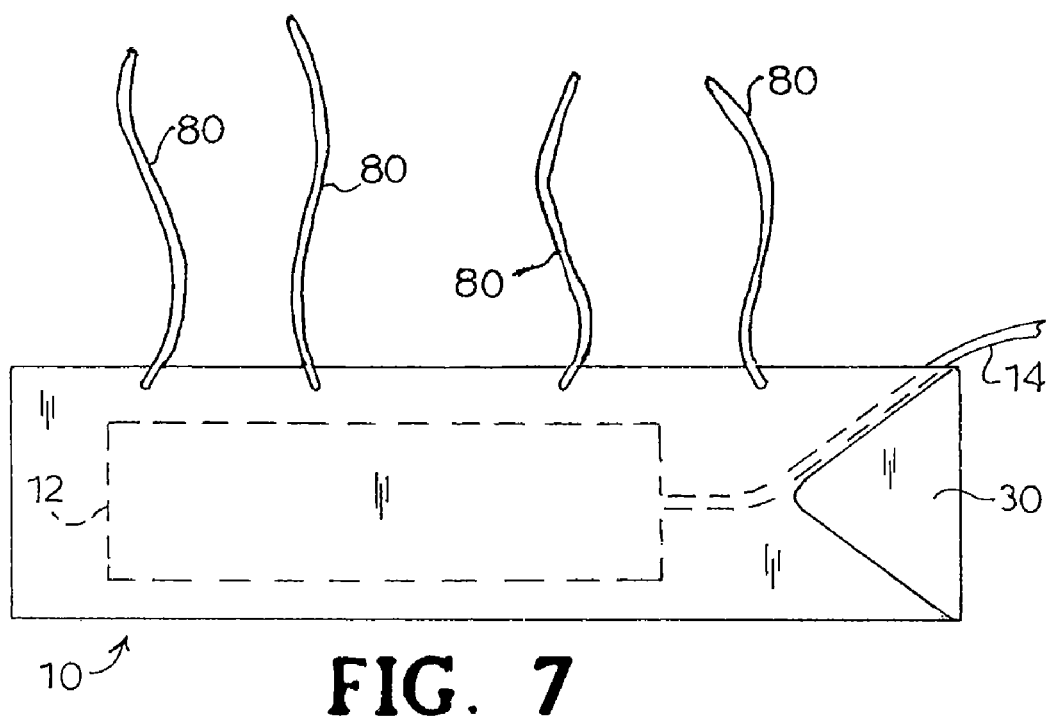
FIG. 7 is a front plan view of another embodiment of the invention as shown in FIG. 3.

FIG. 7 is a view of the pouch 10, showing use of the invention with extensions 80. The pouch 10 has a plurality of extensions 80 that are attached to the pouch at a first end and unattached at a second end in such a way that the extensions can be used to removably secure the pouch 10 to a mammal.

Figure 8:
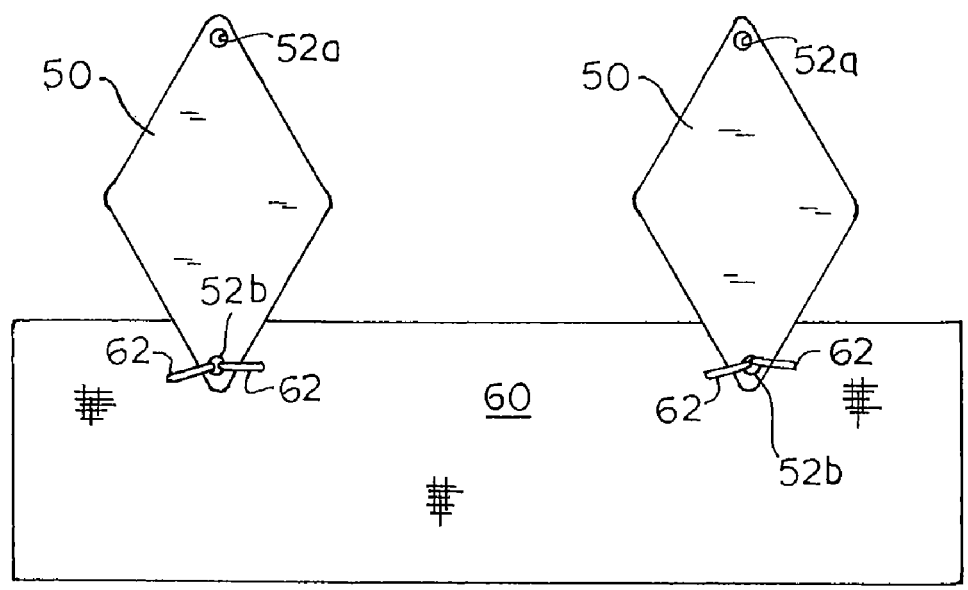
FIG. 8 is a rear plan view of another embodiment of the invention shown with suture wings attached and the pouch flap in the closed position.

FIG. 8 is a view of the pouch 10 of the invention shown with suture wings 50 attached. The pouch 10 shown in FIG. 8 has suture wings 50 attached to the pouch 10 by means of stitches 62 sewn through one of the suture wing openings 52 such that each suture wing 50 is attached to the pouch 10 by stitches 62 through one of its two suture wing openings 52. This leaves the other suture wing opening 52 of each suture wing 50 free so that it may be used to attach the pouch 10 and suture wing 50 to a mammal.

In the preferred embodiment there are three loops attached to the pouch 10 for braiding into the horse's mane, but any number greater than one may be attached. The pouch 10 is ideally attached to a horse's mane, but if needed, the tail of the horse. While the animal being described here is a horse, the pouch 10 could also be used for any other animal with a catheter tube if the hair on the animal is long enough, the device could be attached to the animal's hair by braiding or, alternatively, attached by means of bonding suture wings.

Additionally, the pouch 10 could be used with any mammal, where the loops are braided into the hair of the mammal. If the mammal is a human, the pouch loops could be braided into the hair of the head of the human, or attached by means of suture wings.

In the preferred embodiment, the catheter is a subpalpebral lavage catheter, however any suitable catheter device may be employed, and further, the catheter may be of any type known in the art.

In an alternative embodiment, the pouch has a plurality of extensions of a material similar to that of the loops, except the extension is only attached to the pouch at a first end, instead of looping around to attach to the pouch at a second end. These extensions are removably secured to the hair of the mammal with rubber bands or other suitable device.

In an alternative embodiment, the pouch has a plurality of suture wings, as are known in the art, to removably attach the pouch to the skin of a mammal.

The invention can be further described as comprising:
a) a subpalpebral catheter having a first and a second end wherein said first end is located under the skin of said mammal and said second end further comprises an injection port;
b) a hollow pouch, wherein said pouch has an opening adapted to receive and enclose said injection port of said catheter, wherein said pouch comprises a resilient material;
c) means for closing said opening of said pouch; and
d) a plurality of loops attached to a side of said pouch, spaced apart and of a length wherein said loops are adapted when braided into hair of said mammal to establish an attachment between said side of said pouch and said hair extending for substantially the length of said pouch.

The invention can be further described as comprising:
a) a hollow pouch, having an opening adapted to receive and enclose an injection port of a catheter;
b) means for closing said opening of said pouch; and means for attaching said pouch to said mammal, wherein said means for attaching said pouch to said mammal comprises a plurality of loops attached to a side of said pouch, spaced apart and of a length wherein said loops are adapted when braided into mane hair of said horse to establish an attachment between said side of said pouch and said hair extending for substantially the length of said pouch.

The means for attaching said pouch of the invention to said mammal can be further described as comprising extensions adapted to be removably secured to hair of said mammal.

The means for attaching said pouch of the invention to said mammal can be further described as comprising suture wings.

The invention can be further described as comprising:
a) a subpalpebral catheter having a first and a second end, said first end being located under the skin behind an eye lid of said horse and said second end forming an injection port;
b) a hollow pouch formed of a resilient material and having an opening at one end thereof adapted to receive said injection port for being enclosed therein;
c) means for closing said opening of said pouch; and
d) a plurality of loops attached to a side of said pouch, spaced apart and of a length wherein said loops are adapted when braided into mane hair of said horse to establish an attachment between said side of said pouch and said hair extending for substantially the length of said pouch.

While the invention has been described with regards to specific embodiments, those skilled in the art will recognize that changes can be made in form and detail without departing from the spirit and scope of the invention. This invention is limited only insofar as it is defined by the following claims and includes within its scope all equivalents thereof.

What is claimed is:

1. A catheter device for a mammal comprising:
   a) a catheter having a first and a second end;
   b) a hollow pouch having a length and formed from two layers of a material closed on all sides, the layers defining an interior of the pouch, wherein said pouch has an opening adapted to receive into the interior of the pouch a portion of said catheter including said second end;
   c) means for closing said opening of said pouch such that the portion of said catheter is enclosed within the interior of said pouch and the remaining portion of the catheter, including the first end, extends from the pouch; and
   d) a plurality of cords fixedly attached at their ends along the length of said pouch for forming a plurality of loops attached to said pouch, the plurality of loops spaced apart and of a length wherein said loops are configured to be braided into hair of said mammal to establish an attachment between said pouch and said hair.

2. The catheter protection device of claim 1, wherein the material of said pouch comprises a resilient material.

3. The catheter device of claim 1, wherein said catheter comprises a subpalpebral lavage catheter.

4. The catheter device of claim 1, wherein the plurality of loops are spaced apart such that said plurality of loops extend for substantially the length of said pouch.

5. The catheter device of claim 1, wherein the first end of the catheter is adapted to be located under skin of said mammal.

6. The catheter device of claim 1, wherein the second end of the catheter comprises an injection port adapted to be received and enclosed within the interior of said pouch.

7. The catheter device of claim 1, wherein the closing means comprises a flap integral with the pouch, the flap moveable between a first open position wherein the flap extends away from the opening of said pouch and a second closed position wherein the flap is adjacent an outer surface of the pouch and over the opening of said pouch for closing said opening.

8. The catheter device of claim 1, wherein the length of the loops is about 2 inches.

9. A device for a mammal for protecting a catheter for transmitting fluids and having a first end and a second end, the catheter protection device comprising:
   a) a hollow pouch formed from two layers of a material closed on all sides, the layers defining an interior of the pouch and having an opening adapted to receive into the interior of the pouch a portion of said catheter including said second end;
   b) means for closing said opening of said pouch such that the portion of said catheter is enclosed within the interior of said pouch and the remaining portion of the catheter, including the first end, extends from the pouch; and
   c) means for attaching said pouch to said mammal.

10. The catheter protection device of claim 9, wherein said pouch comprises a resilient material.

11. The catheter protection device of claim 9, wherein said means for attaching said pouch to said mammal comprises a plurality of loops attached to said pouch, the plurality of loops spaced apart and of a length wherein said loops are configured when braided into hair of said mammal to establish an attachment between said pouch and said hair.

12. The catheter protection device of claim 11, wherein the plurality of loops are spaced apart such that said plurality of loops extend for substantially the length of said pouch.

13. The catheter protection device of claim 11, wherein the length of the loops is about 2 inches.

14. The catheter protection device of claim 9, wherein said means for attaching said pouch to said mammal comprises extensions adapted to be removably secured to hair of said mammal.

15. The catheter protection device of claim 9, wherein said means for attaching said pouch to said mammal comprises suture wings.

16. The catheter protection device of claim 15, wherein said suture wings are secured to said pouch and wherein said suture wings are adapted to be secured to body of said mammal.

17. The catheter protection device of claim 15, wherein said suture wings are adapted to be secured to body of said mammal and wherein means for attaching said pouch to said mammal comprises means for securing said pouch to said suture wings.

18. The catheter protection device of claim 17, wherein means for securing said pouch to said suture wings comprises a plurality of cords fixedly attached at their ends along the length of said pouch for forming a plurality of loops.

19. The catheter protection device of claim 9, wherein the closing means comprises a flap integral with the pouch, the flap moveable between a first open position wherein the flap extends away from the opening of said pouch and a second closed position wherein the flap is adjacent an outer surface of the pouch and over the opening of said pouch for closing said opening.

20. A catheter device for a horse comprising:
   a) a catheter having a first and a second end;
   b) a hollow pouch having a length and formed from two layers of material colosed on all sides, the layers defining an interior of the pouch, the pouch having an opening adapted to receive into the interior of the pouch a portion of said catheter including said second end;
   c) means for closing said opening of said pouch such that the portion of said catheter is enclosed within the interior of said pouch and the remaining portion of the catheter, including the first end, extends from the pouch; and
   d) a plurality of cords fixedly attached at their ends along the length of said pouch for forming a plurality of loops attached to said pouch, the plurality of loops spaced apart and of a length wherein said loops are configured when braided into mane hair of said horse to establish an attachment between said pouch and said hair.

21. The catheter device of claim 20, wherein the material of said pouch comprises a resilient material.

22. The catheter device of claim 20, wherein the plurality of loops are spaced apart such that said plurality of loops extend for substantially the length of said pouch.

23. The catheter device of claim 20, wherein the first end of the catheter is adapted to be located under skin of said mammal.

24. The catheter device of claim 20, wherein the second end of the catheter comprises an injection port adapted to be received and enclosed within the interior of said pouch.

25. The catheter device of claim 20, wherein the catheter comprises a subpalpebral lavage catheter.

26. The catheter device of claim 20, wherein the closing means comprises a flap integral with the pouch, the flap moveable between a first open position wherein the flap extends away from the opening of said pouch and a second closed position wherein the flap is adjacent an outer surface of the pouch and over the opening of said pouch for closing said opening.

27. The catheter device of claim 20, wherein the length of the loops is about 2 inches.

28. A method for transmitting fluid to or from a mammal comprising:
   a) providing a catheter having a first and a second end;
   b) providing a hollow pouch formed from two layers of a material closed on all sides, the layers defining an interior of the pouch, wherein said pouch has an opening adapted to receive into the interior of the pouch a portion of said catheter including said second end and wherein said pouch has a means for removably attaching said pouch to said mammal;
   c) providing a means for closing said opening of said pouch such that the portion of said catheter is enclosed within said pouch and the remaining portion of the catheter, including the first end, extends from the pouch; and
   d) removably securing said pouch to said mammal to establish an attachment between said pouch and said mammal.

29. A method for protecting a catheter attached to a mammal, the catheter having a first end and a second end, the method comprising:
   a) providing a hollow pouch formed from two layers of a material closed on all sides, the layers defining an interior of the pouch, wherein said pouch has an opening adapted to receive into the interior of the pouch a portion of said catheter including said second end and wherein said pouch has a mains for removably attaching said pouch to said mammal;
   b) providing a means for closing said opening of said pouch such that the portion of said catheter is enclosed within said pouch and the remaining portion of the catheter, including the first end, extends from the pouch; and
   c) removably securing said pouch to said mammal to establish an attachment between said pouch and said mammal.

* * * * *

UNITED STATES PATENT AND TRADEMARK OFFICE
CERTIFICATE OF CORRECTION

PATENT NO. : 7,632,255 B2 Page 1 of 1
APPLICATION NO. : 11/208118
DATED : December 15, 2009
INVENTOR(S) : Andrea H. Selch It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 366 days.

Signed and Sealed this

Second Day of November, 2010

David J. Kappos
*Director of the United States Patent and Trademark Office*